United States Patent
Pidria et al.

(10) Patent No.: US 7,257,984 B2
(45) Date of Patent: Aug. 21, 2007

(54) MINIATURIZED SENSOR DEVICE FOR DETECTING CHARACTERISTICS OF A FLUID, IN PARTICULAR A LUBRICATING OIL

(75) Inventors: Marco Federico Pidria, Orbassano (IT); Marco Pizzi, Orbassano (IT); Paolo Faraldi, Orbassano (IT); Edoardo Merlone Borla, Orbassano (IT); Silvio Corrias, Orbassano (IT); Gianfranco Innocenti, Orbassano (IT)

(73) Assignee: C.R.F. Societa Consortile per Azioni, Orbassano (Turin) (IT)

( * ) Notice: Subject to any disclaimer, the term of this patent is extended or adjusted under 35 U.S.C. 154(b) by 113 days.

(21) Appl. No.: 11/312,639

(22) Filed: Dec. 21, 2005

(65) Prior Publication Data

US 2006/0130562 A1    Jun. 22, 2006

(30) Foreign Application Priority Data

Dec. 22, 2004    (EP)    ................... 04425938

(51) Int. Cl.
  *G01N 11/10*    (2006.01)
  *G01N 33/30*    (2006.01)
(52) U.S. Cl. .................. 73/10; 73/9; 73/53.05; 73/54.24; 73/54.26; 73/64.53
(58) Field of Classification Search .............. 73/9, 73/10, 53.05, 53.01, 54.23, 54.24, 54.25, 73/54.26, 54.39, 54.41, 64.53
See application file for complete search history.

(56) References Cited

U.S. PATENT DOCUMENTS

| | | | |
|---|---|---|---|
| 4,966,032 A | 10/1990 | Takeuchi | |
| 5,825,119 A * | 10/1998 | Shibata et al. | 310/338 |
| 5,918,354 A * | 7/1999 | Ikegami et al. | 29/25.35 |
| 6,023,961 A | 2/2000 | Discenzo et al. | |
| 6,269,685 B1 * | 8/2001 | Oden | 73/54.23 |
| 6,289,717 B1 * | 9/2001 | Thundat et al. | 73/23.2 |
| 7,043,969 B2 * | 5/2006 | Matsiev et al. | 73/54.41 |
| 7,162,918 B2 * | 1/2007 | DiFoggio et al. | 73/152.32 |
| 7,178,378 B2 * | 2/2007 | Crawley et al. | 73/24.06 |
| 7,210,332 B2 * | 5/2007 | Kolosov et al. | 73/24.06 |
| 2002/0053532 A1 * | 5/2002 | Quake et al. | 209/2 |
| 2002/0194906 A1 * | 12/2002 | Goodwin et al. | 73/152.46 |
| 2003/0041659 A1 * | 3/2003 | Marszalek et al. | 73/119 R |
| 2004/0250606 A1 | 12/2004 | Buttgenbach et al. | |
| 2004/0250622 A1 * | 12/2004 | Kolosov et al. | 73/570 |

(Continued)

FOREIGN PATENT DOCUMENTS

EP    0 675 355    10/1995

(Continued)

*Primary Examiner*—Hezron Williams
*Assistant Examiner*—David A. Rogers
(74) *Attorney, Agent, or Firm*—Nixon & Vanderhye P.C.

(57) ABSTRACT

A miniaturized sensor device comprises at least one pair of active projecting elements or cantilevers, which are set parallel to one another and at a micrometric or sub-micrometric distance apart and are designed to be submerged at least partially in a fluid. Each pair comprises a first cantilever, equipped with actuator means, and a second cantilever, equipped with sensor means. The actuator means can cause a movement of the first cantilever, whilst the sensor means can detect a movement of the second cantilever, induced by the movement of the first cantilever, for generating accordingly a measurable signal, which represents the lubricating capacity of the fluid.

22 Claims, 2 Drawing Sheets

U.S. PATENT DOCUMENTS

2005/0034542 A1* 2/2005 Thaysen ................ 73/862.634
2005/0145019 A1* 7/2005 Matsiev et al. ............ 73/53.01
2005/0262944 A1* 12/2005 Bennett et al. ............... 73/592
2007/0089515 A1* 4/2007 Shih et al. .................... 73/579

FOREIGN PATENT DOCUMENTS

WO    WO 02/090941    11/2002

* cited by examiner

MINIATURIZED SENSOR DEVICE FOR DETECTING CHARACTERISTICS OF A FLUID, IN PARTICULAR A LUBRICATING OIL

BACKGROUND OF THE INVENTION

The present invention relates to a miniaturized device for the detection of characteristics of a fluid. The device according to the invention finds advantageous, even though not exclusive, application in the measurement of performance of a lubricating oil, directly on a system or an apparatus that uses the oil itself, such as for example an internal-combustion engine.

By now widely shared is the conviction that only a simultaneous measurement of many parameters enables a satisfactory characterization of the conditions of wear and contamination of a lubricating oil. Amongst said parameters of particular importance is the lubricating capacity of the oil.

In the laboratory, the oils can be conveniently tested using tools dedicated thereto, referred to as tribometers, which are able to measure quantitatively the characteristics of lubricating efficiency of the oils. On systems and apparatuses that use lubricating oils, such as an internal-combustion engine, the characteristics of the oils are instead detected via appropriate sensor devices. Said devices are generally designed to deduce conditions of wear and contamination of the lubricating oils on the basis of the measurement of parameters such as viscosity, temperature, conductivity, opacity, dielectric constant, just to mention the ones most widely taken into consideration.

The patent document No. U.S. Pat. No. 4,966,032 describes a instrument for monitoring a lubricating oil, equipped with supporting means that comprise a basic body, which has a surface of contact that can be submerged in the lubricating oil. Associated to the basic body is a lamina-like element, which can be set in vibration and has a portion of contact that rests on the aforesaid surface of contact. Associated to the lamina-like element are actuator means, designed to cause vibration of the lamina-like element, and sensor means for detecting a vibration of the lamina itself caused by the friction between said portion and the surface of contact to produce an output signal of the sensor. The sensor means and the actuator means are made of piezoelectric material.

The patent document No. EP-A-0 675 355 describes a sensor element for detecting solid particles in a fluid, such as a lubricating oil, comprising a cantilever element of dimensions such as to enable its vibration following upon a collision with a solid particle, and means for converting a vibration of the cantilever element into an electrical signal. The aforesaid means are formed by a film made of piezoelectric material. A possible embodiment envisages the use of a plurality of cantilever elements, a first one of which is used as sensor for detecting the solid particles and a second one of which is used as sensor to obtain a reference parameter necessary for the purposes of the measurement. A third cantilever element can possibly be set in vibration via the respective piezoelectric means (by inverse piezoelectric effect), so as to exploit said vibration for the purposes of detecting the degree of viscosity of the fluid.

Notwithstanding the vast literature on the subject, there has not yet been proposed a miniaturized sensor for monitoring the conditions of lubricating efficiency of a generic fluid, such as an oil.

SUMMARY OF THE INVENTION

The present invention has the aim of overcoming said drawback and in particular to indicate a miniaturized device that enables direct measurement of the performance of a fluid in terms of lubricating capacity, i.e., of its effects on the modification of the coefficient of dynamic friction in controlled conditions.

Another purpose of the invention is to provide such a device that meets the requirements for an effective use on motor vehicles, for the purposes of monitoring the characteristics of an oil.

According to the present invention, said purposes are achieved thanks to a miniaturized sensor device having the characteristics referred to specifically in the annexed claims, which form an integral part of the descriptive contents of the present patent application.

BRIEF DESCRIPTION OF THE INVENTION

Further purposes, characteristics and advantages of the present invention will emerge clearly from the ensuing detailed description and from the annexed plate of drawings, which are provided purely by way of explanatory and non-limiting example, and in which.

DETAILED DESCRIPTION OF THE INVENTION

The sensor device forming the subject of the present invention is devised for reproducing in microscale the typical conditions, in terms of geometry and forces, of a lubricated tribological coupling.

For said purpose, according to the principal aspect of the invention, the sensor device comprises one or more pairs of projecting elements, also defined hereinafter as cantilever elements, which are adjacent to one another and are set at a controlled distance from one another. The two cantilevers of each pair are as similar as possible to one another, with one cantilever element equipped with actuation means, designed to generate a controlled oscillation of the cantilever itself, and the other cantilever element equipped with means for detection of the oscillation generated by the first cantilever element. The oscillation of the cantilevers is induced for the time necessary to obtain an appropriate measurement.

A single pair of cantilevers is theoretically sufficient to obtain the desired measurement. The presence of a number of pairs is, however, preferable in order to obtain a value characterized by a more favourable signal-to-noise ratio.

Preferably, the actuator means and the means of detection are made of an active material, such as a piezoelectric material, preferably of a polarized type.

Figure 1:
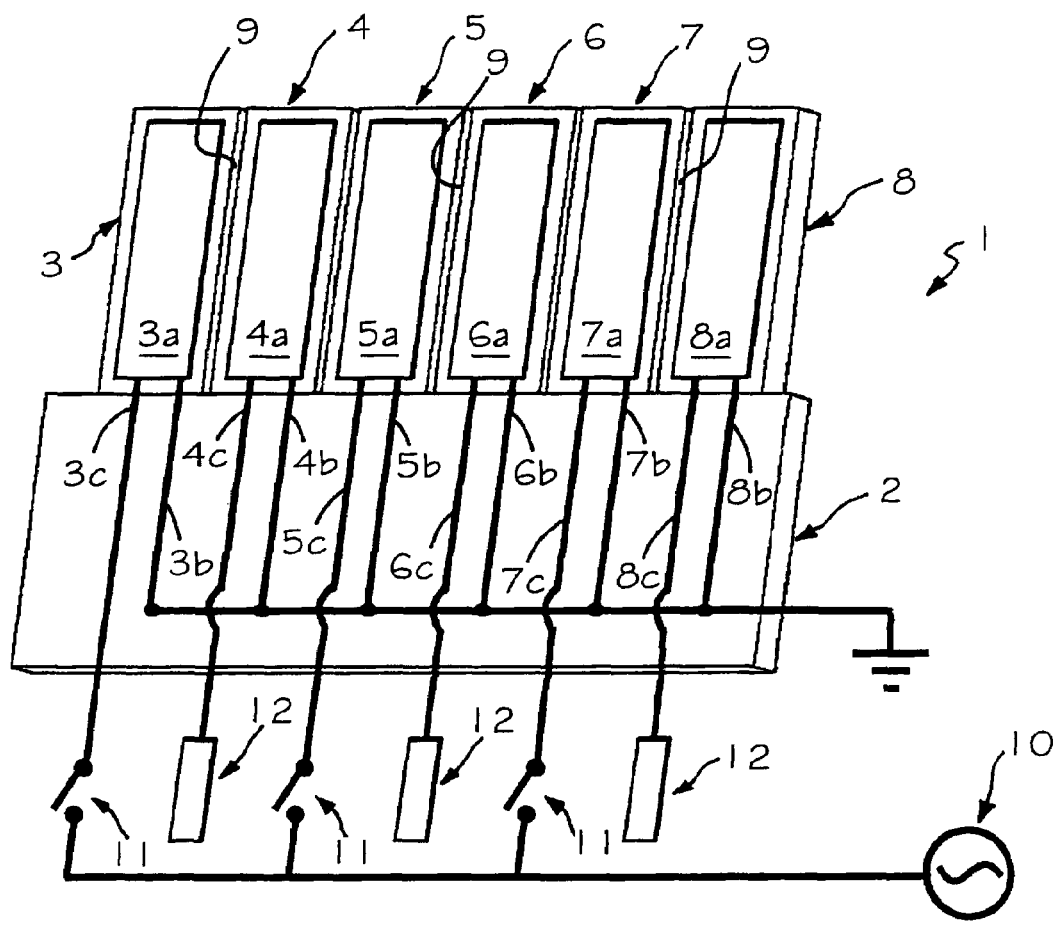
FIG. 1 is a perspective schematic view of a sensor device, in accordance with a first embodiment of the invention.

In FIG. 1, designated as a whole by 1 is a miniaturized sensor device made in accordance with the invention.

The device 1 comprises a supporting part, designated by 2, from which there extends a series of flexible projecting elements, or cantilevers, set parallel to one another and designated by the reference numbers from 3 to 8. In the case exemplified, the device 1 envisages six cantilever elements, and hence three pairs of cantilevers 3-4, 5-6 and 7-8.

The cantilevers 3-8 of each pair are as similar as possible to one another, preferably shaped like a substantially parallelepipedal lamina, having dimensions of the order of 0.5-5 mm (length), 200 µm-1 mm (width), and 50-500 µm (depth or thickness).

The cantilevers 3-8 of each pair are set adjacent to one another, at a controlled distance from one another, in the region of some hundreds of micron to some tens of micron. In this way, between the mutually facing surfaces of the two cantilevers of the same pair there are formed areas of sliding 9 (note that, in the figures, the dimensions of the areas 9 have been deliberately exaggerated).

On at least one of the two larger surfaces of each cantilever 3-8 there is set a respective element made of active material, preferably in the form of a layer or film. Said layers of active material are designated in the figures by the reference numbers from 3a to 8a. In the preferred embodiment of the invention, the layers 3a-8a are made of piezoelectric material, and have a thickness of the order of 20-300 µm.

As is known, piezoelectricity is the capacity for some crystalline materials to manifest an electrical charge if subjected to mechanical stresses, or else to undergo deformation if subjected to an electrical field. Both of the effects mentioned, known as direct piezoelectric effect and inverse piezoelectric effect, are exploited for the purposes of implementation of the present invention, as will emerge clearly from what follows.

More in particular, the piezoelectric layers 3a, 5a and 7a are used for generating an oscillation or controlled vibration of the respective cantilevers 3, 5 and 7, substantially in the direction perpendicular to their normal plane of lie. For this purpose, the inverse piezoelectric effect is exploited. The piezoelectric layers 4a, 6a and 8a are, instead, used as sensors, which can detect external mechanical stresses, however generated, to which the respective cantilevers 4, 6 and 8 are subjected. For this purpose, the direct piezoelectric effect is exploited.

Associated to the piezoelectric layers 3a-8a are first electrodes 3b-8b, connected to a common ground. Associated to the piezoelectric layers 3a, 5a and 7a are second electrodes 3c, 5c and 7c, for connection to an alternating or pulsed voltage source of appropriate frequency, typically comprised between some kHz and some tens of MHz, designated by 10, with interposition of respective controlled switching means, designated by 11, the components 10 and 11 being of a conception in itself known. Associated to the piezoelectric layers 4a, 6a and 8a are second electrodes 4c, 6c and 8c, for the connection to respective measuring circuits 12. Also the measuring circuits 12 are of a conception in itself known and can each for example comprise an amplifier, a high-pass filter and a voltmeter.

The use of the device 1 according to the invention in combination with an engine requires of course the use of solutions designed to remove the vibrational components induced by the operation of the engine itself. The ranges of frequency involved are, however, very different, so that the separation of the signal of interest may be obtained with an appropriately designed filtering, in itself clear to persons skilled in the sector.

It may be noted that, instead of three distinct supply circuits and three distinct measuring circuits, the device 1 could comprise a single circuit for simultaneous supply of the piezoelectric layers 3a, 5a and 7a, and a single circuit for measuring the mechanical stresses exerted on the piezoelectric layers 4a, 6a and 8a.

Figure 2:
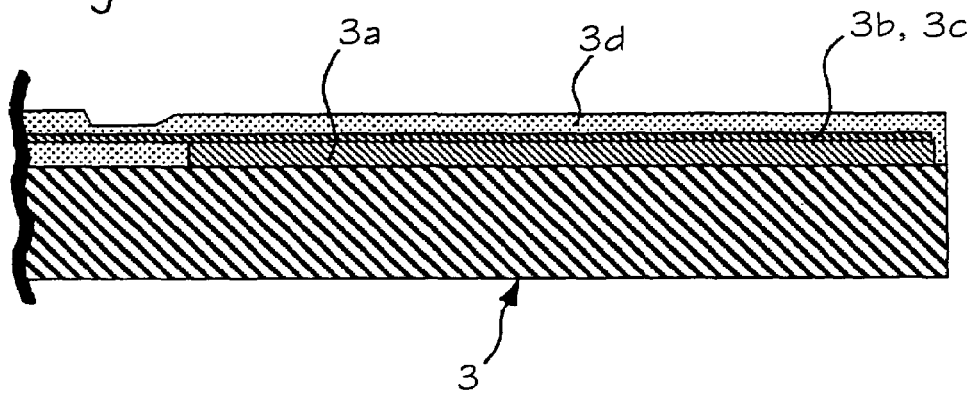
FIG. 2 is a schematic cross-sectional view of a cantilever element used in sensor devices according to the invention.

FIG. 2 represents, with a schematic cross-sectional view, a possible structure of the cantilever 3, taking for granted that the other cantilevers 4-8 are similar.

The cantilever 3 may, for example, be made of aluminium oxide ($Al_2O_3$) or silicon. On the substrate constituted by the cantilever 3 is deposited the layer of piezoelectric material 3a, for example PZT, or PT, or more complex mixtures of oxides, including recently developed ones, with low or zero lead content. Next, there are deposited the electrodes 3b, 3c, for example made of Pt, Pd, Ag or mixtures of these metals appropriately prepared and used in the form of serigraphic pastes, which are also in the form of a conductive layer or film. There is then applied an insulating coating 3d, for example formed by a serigraphable film or layer with low dielectric constant (note that the insulating layer 3d has not been represented in FIGS. 1 and 3 for reasons of greater clarity). The electrodes of the various cantilevers may be positioned in various ways, according to the constructional design chosen (for example, on top of the piezoelectric layer, at its sides, one on top and the other underneath, etc.).

As previously mentioned, in each of the aforesaid pairs, one cantilever 3, 5, 7 with the respective piezoelectric layer 3a, 5a, 7a is used as actuator, whilst the adjacent or facing cantilever 4, 6, 8 with the respective piezoelectric layer 4a, 6a, 8a functions as sensor of the stress generated by the actuator cantilever.

In use, at least the cantilevers 3-8 of the device 1 are submerged in a bath of the fluid of which it is desired to monitor the lubricating capacity, such as for example the oil of an internal-combustion engine.

In idle conditions; i.e., where a voltage to the piezoelectric layers 3a, 5a, 7a is not supplied, the cantilevers 3-8 are substantially parallel to one another, as visible in FIG. 1. When the switching means 11 is closed, this causes a voltage to the respective piezoelectric layers 3a, 5a, 7a. Following upon the controlled application of the voltage to the layer 3a, 5a, 7a, this is deformed, oscillating, according to the inverse piezoelectric effect, thereby causing a cyclic deformation of the corresponding actuator cantilever 3, 5, 7. Said deformation basically determines an arching or curving of the actuator cantilever, and hence an oscillation thereof, which occurs substantially in the direction perpendicular to the normal plane of lie of the cantilever itself.

In this way, the lateral surface of the actuator cantilever, which delimits on one side the space 9, tends to move with respect to the lateral surface of the adjacent sensor cantilever 4, 6, 8 that delimits the space 9 on the opposite side. In effect, then, the aforesaid surface of the actuator cantilever, as it moves, slides on the facing surface of the sensor cantilever. Given the micrometric or sub-micrometric dimensions of the areas 9, the sensor cantilever 4, 6, 8 is in any case stressed.

It may be noted that it is also possible to apply a normal load on the side surfaces of the cantilevers, so as to control the tribological coupling in a rigorous way. Said load can be obtained via electrodes that are additional to the ones represented, appropriately placed with respect to the piezoelectric layer, or else simply by obtaining deformations of the piezoelectric layer in a number of directions using the same electrodes described above (for example, exploiting the modes or piezoelectric constants $d_{31}$ and $d_{33}$), which are able to stress an appropriate flexural mode, with a d.c.

voltage applied throughout the time of activation of the oscillations of the cantilever or with an appropriately synchronized pulsed signal.

As emerges, then, via the piezoelectric layers 3a, 5a, 7a it is possible to apply a known and controlled force between the facing surfaces of the cantilevers of each pair.

The energy transmitted by an actuator cantilever 3, 5, 7 to the respective sensor cantilever 4, 6, 8 will depend upon:

the normal load, which forces the adjacent surfaces of the two cantilevers against one another in a position corresponding to the respective area of sliding 9; and the medium, i.e., the fluid or oil, in which the device 1 is at least partially submerged, and in particular its lubricating properties.

For the above purpose, the geometry of the facing surfaces of the actuator cantilevers and sensor cantilevers of a pair, also in terms of roughness, and the corresponding distance are controlled with sub-micrometric precision for enabling a sufficient repeatability in the performance of the device 1. As has been said, the piezoelectric layers can also be pre-arranged to impose a controlled load in the direction normal to that of oscillation.

The distance and load may be defined according to the characteristics of the surfaces set sliding in the system which uses the fluid that it is desired to monitor via the device 1. In other words, the device 1 can be devised for simulating, for example, a tribological coupling of a cylinder/ring/piston type of an engine, even though the device itself is operatively positioned in another point of the oil circuit, for example in the proximity of a sump.

As has been explained, the amount of mechanical stress that is transferred from the actuator cantilever 3, 5, 7 to the sensor cantilever 4, 6, 8 is a function of the lubricating capacity of the fluid. Consequently, the greater the lubricating capacity of the fluid, the smaller will be the stress transmitted to the sensor cantilever, and vice versa.

The stress transmitted to the sensor cantilever brings about an oscillation of the cantilever itself, which is transmitted to the respective piezoelectric layer 4a, 6a, 8a. The consequent deformation of the piezoelectric layer 4a, 6a, 8a causes the latter to generate a voltage, as a direct piezoelectric effect. Said voltage is detected through the respective measuring circuit 12, which, as mentioned, can for said purpose comprise a voltmeter or similar means for measuring the voltage.

The amount of the voltage measured by the circuit 12 thus represents the oscillation or stress imparted on the sensor cantilever by the respective actuator cantilever, which is in turn a function of the lubricating capacity of the oil. As may be imagined, the greater the lubricating capacity of the fluid, the smaller the stress transmitted to the sensor cantilever, and hence the smaller will be the amount of the voltage generated by its piezoelectric layer, which may be detected by the respective circuit 12. Instead, the smaller the lubricating capacity of the fluid, the greater will be the stress transmitted to the sensor cantilever, and hence the greater the amount of the voltage generated by its piezoelectric layer, which may be detected by the respective circuit 12.

On the basis of the value detected by the circuit 12, the control system to which the device 1 is interlocked is able to carry out the direct measurement 5 of the lubricating capacity of the fluid, i.e., of the coefficient of dynamic friction, between the actuator cantilever 3, 5, 7 and the sensor cantilever 4, 6, 8. The control system of the device 1 is for this purpose pre-arranged for coordinating with one another execution of the controlled movement of the actuator cantilever 3, 5, 7 and the evaluation, according to the amount of the consequent stress of the sensor cantilever 4, 6, 8, of the value representing the characteristic quantity of interest of the fluid F. For the purposes of said evaluation, a suitable known processing technique, for example of the type that uses algorithms of calculation proper to fuzzy logic, can be used.

Figure 3:
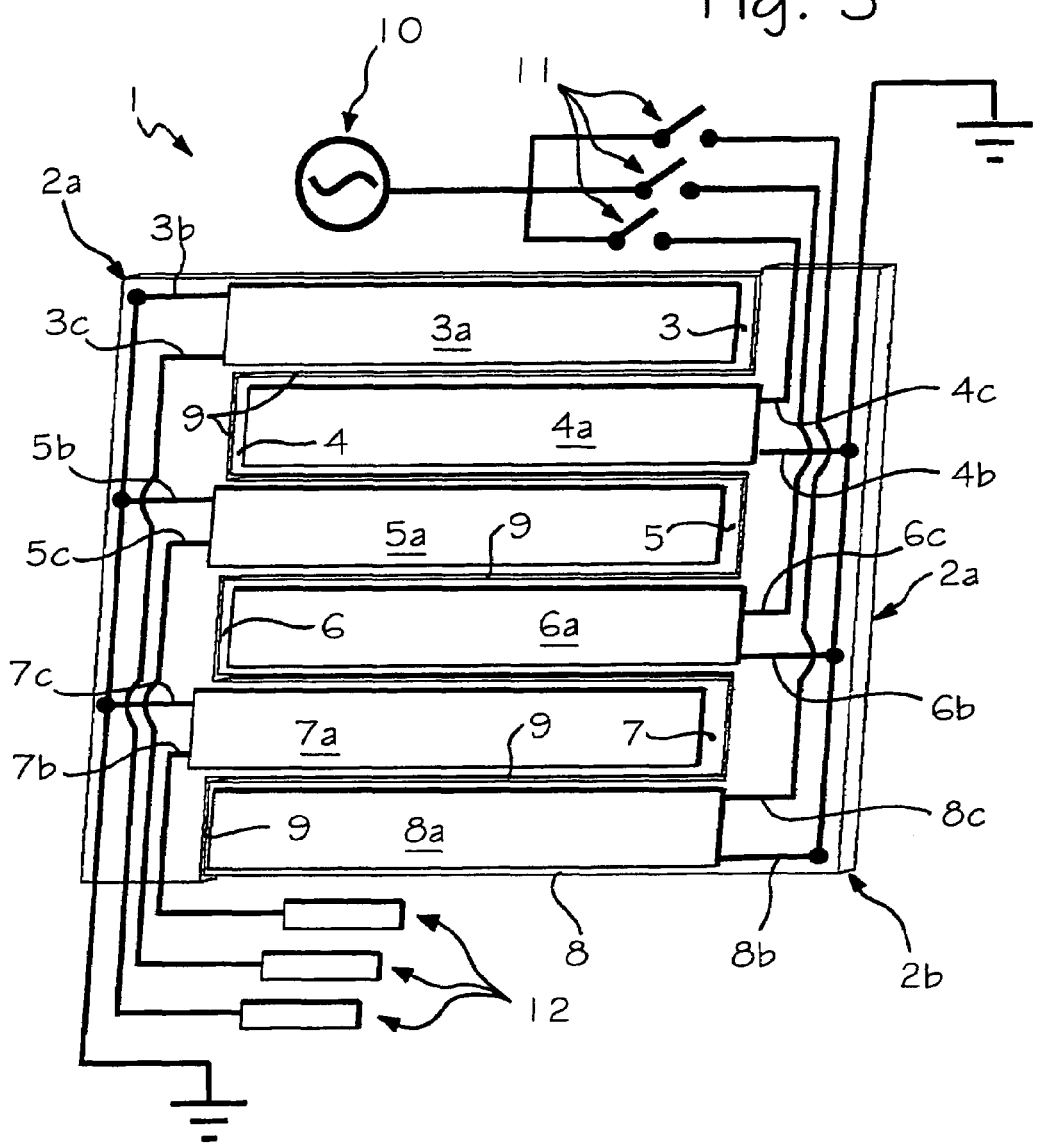
FIG. 3 is a perspective schematic view of a sensor device, in accordance with a second embodiment of the invention.

FIG. 3 illustrates a possible variant embodiment of the invention, in accordance with which the actuator cantilevers 3, 5, 7 and the sensor cantilevers 4, 6, 8 are arranged according to an interdigitated configuration. In said, figure the same reference numbers as those of FIG. 1 are used to indicate elements that are technically equivalent to the ones already described above.

As emerges, in the embodiment of FIG. 3 there are envisaged two substantially comb-like supporting parts, designated by 2a and 2b, the teeth of which provide respective cantilevers. The cantilevers 3, 5, 7, with the respective piezoelectric layers 3a, 5a, 7a of the element 2a perform the functions of actuator, whilst the cantilevers 4, 6, 8, with the respective piezoelectric layers 4a, 6a, 8a of the element 2b, perform the functions of sensor. The positions of the two elements 2a, 2b with respect to one another is such that the cantilevers 3, 5, 7 of one are interspersed with the cantilevers 4, 6, 8 of the other, to assume the desired interdigitated configuration.

Operation of the device 1 in the version of FIG. 3 is similar to the one previously described. Given the aforesaid interdigitated configuration, in this embodiment, part of the areas of sliding 9 are formed also between the front surfaces of the actuator cantilevers 3, 5, 7 (or sensor cantilevers 4, 6, 8) and the front surface of the element 2a (or 2b) that is located between two sensor cantilevers 4, 6, 8 (or actuator cantilevers 3, 5, 7). This enables an increase in the resolution of measurement of the device 1.

Obviously, also in this embodiment the areas of sliding 9 will be delimited by surfaces set at a controlled distance apart, typically micrometric or sub-micrometric, in a position substantially parallel in the inoperative conditions of the device 1.

In the variant of FIG. 3, the cantilevers 3-8 are made of a single piece with the corresponding supporting parts 2a, 2b. A similar embodiment could be used also in the case of FIG. 1, i.e., providing all the cantilevers 3-8 of a single piece with the respective common supporting part 2.

As has already been explained, the geometry of the facing surfaces of the actuator cantilevers and sensor cantilevers and the corresponding distance must be controlled with extreme precision. For said purpose, a possible technique that can be used for the production of the cantilevers 3-8, both in the configuration of FIG. 1 and in that of FIG. 2, is the one known as "deep reactive ion etching" (DRIE). The piezoelectric layers 3a-8a and the electrodes 3b-8b and 3c-8c can be deposited with classic serigraphic techniques or with high-resolution techniques, such as for example "gravure printing". The protective layer 3d of FIG. 2 can be deposited via techniques similar to what has been described previously.

Preferably, for the purposes of the formation of the piezoelectric layers 3a-8a, ferro-electrical materials of a "soft" or "relaxor" type are used, which enable operation also outside resonance.

In the configurations exemplified, the piezoelectric layers 4a, 6a, 8a of the sensor cantilevers 4, 6, 8 preferably exploit the direct piezoelectric constant known as "$d_{31}$", for the purposes of the generation of voltage detectable by the circuit 12. In possible variant embodiments, for said purpose the piezoelectric constant known as "$d_{51}$" could instead be exploited.

Figure 4:
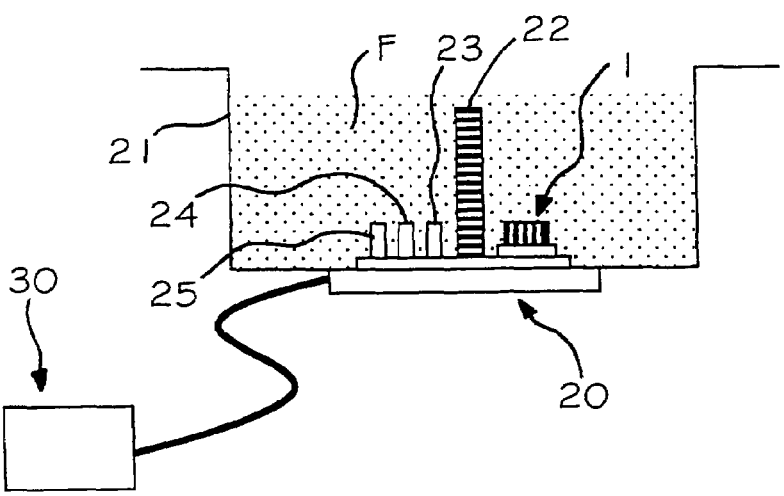
FIG. 4 is a schematic view of a possible use of the sensor device according to the invention.

In practical use, the device 1 according to the invention can form part of a detection arrangement that comprises various sensor means, of a type in itself known, for the purposes of the evaluation of other characteristics of the fluid of interest. FIG. 4 exemplifies a possibility in this sense, in accordance with which there is provided a detector device, designates as a whole with 20, mounted in a position corresponding to a sump 21 of the oil F of an internal-combustion engine. The device 20 integrates both the sensor 1 previously described and sensor means 22-24, of a type in itself known, for sensing variables such as the dielectric constant, the electrical conductivity, the transmittance/absorbance, and the viscosity of the oil. Advantageously, there can also be envisaged sensor means 25 for detecting the temperature of the oil F.

The variable detected by the sensor means 25, in addition to having importance in absolute terms (i.e., as regards knowledge of the temperature of the oil) is also used for the purpose of "compensating" any detection made by means of one or more of the other sensors 1 and/or 22-24; in fact, certain physical characteristics of the oil can vary at different temperatures of the fluid (for example, the value of viscosity of the oil at a first temperature is different from the value detectable at a different operating temperature of the same fluid). To the device there can in any case be associated means for controlling and stabilizing the temperature of the fluid being evaluated by the sensor, such as heating and/or cooling means. For example, the device 1 can be operatively positioned in a respective shell or chamber, branching off from the hydraulic circuit and hence designed to receive a sample of the fluid to be analysed. Associated to said chamber is a thermostated heater, that is able to bring the fluid up to a predetermined temperature, and, when it is reached, the device 1 will carry out detection using the operating modes described above.

Purely by way of example:

the sensor means 22 for detecting the dielectric constant and/or conductivity can be of a capacitive type;

the sensor means 23 for detecting the transmittance/absorbance can be of an optical type;

the sensor means 24 for detecting the viscosity can be of the type that uses a quartz oscillator;

the sensor means 25 for detecting the temperature can be of the type that uses a negative-temperature-coefficient (NTC) resistor.

The device 20 is connected to a control unit 30 for the signals detected by the various sensor means 1, 22-25, for processing the signals themselves. The one or more switching means 11 and/or circuits 12 can be integrated in said unit 30.

Of course, without prejudice to the principle of the invention, the details of construction and the embodiments may vary with respect to what is described and illustrated herein purely by way of example.

For example, if it is deemed necessary, a piezoelectric layer, with the corresponding electrodes and insulating/protective coating, could be associated also to the underside face of the cantilevers 3-8.

The invention has been previously described with reference to the use of a piezoelectric material for the purposes of fabrication of the actuator 3a, 5a, 7a and sensors 4a, 6a, 8a layers. In possible variant embodiments, however, said layers could be formed with another active material, or combinations of a number of active materials. There is pointed out in particular the possibility of using a magnetostrictive material. In this case, the magnetostrictive layers applied to the actuator cantilevers will be excitable by a magnetic field, in order to cause their deformation. The amount of the subsequent deformation induced in the sensor cantilevers, and hence in the corresponding magnetostrictive layers, may be detected on the basis of the inverse magnetostrictive effect.

In further variant embodiments, the cantilevers 3-8 could be entirely made of active material, without the need to envisage the respective layers 3a-8a, for example of piezoelectric material or magnetostrictive material.

What is claimed is:

1. A miniaturized sensor device for the detection of at least one characteristic quantity of a fluid; particularly a lubricating oil, comprising:

2N cantilever elements arranged at least partially exposed to said fluid or submerged therein, where N is a whole number;

actuating means to cause at least one first cantilever element to perform controlled movements;

wherein said at least one first cantilever element is adapted to perform controlled movements in response to said actuating means and at least one second cantilever element arranged to have a separating distance relative to said at least one first cantilever element such that a deformation of the first cantilever element in response to said actuating means induces a deformation of said at least one second cantilever element, said induced deformation generating a stress in said at least one second cantilever element that is related to said characteristic quantity;

sensing means to detect said generated stress in said second cantilever element; and control means for executing said controlled movement of the first cantilever element and the evaluation of a value which is representative of said characteristic quantity as a function of said stress.

2. The device according to claim 1, wherein said characteristic quantity is the lubricating capacity of the fluid and is determined by calculating the coefficient of dynamic friction between the first cantilever element and the second cantilever element as a function of the stress.

3. The device according to claim 1, wherein said actuating means is electrical or magnetic.

4. The device according to claim 1, wherein each of the cantilever elements are coupled to a common support component from which they extend in substantially parallel positions.

5. The device according to claim 1, wherein the cantilever elements are arranged according to an interdigital configuration, wherein one or more first cantilever elements are coupled to a first support component and one or more second cantilever elements coupled to a second support component.

6. The device according to claim 1, wherein said device is part of an arrangement for detecting of at least one further characteristic of the fluid selected from the group consisting of a dielectric constant, electrical conductivity, transmittance/absorbance, viscosity, and temperature.

7. The device according to claim 1, wherein there is provided a plurality of pairs of cantilever elements, each of said pairs comprising a first cantilever element and a second cantilever element.

8. The device, according to claim 1, further comprising means for heating and/or cooling the fluid for controlling and/or stabilizing the temperature of a volume of the fluid to which the first and second cantilever elements are at least partially exposed or submerged.

9. The device according to claim 1 wherein each cantilever element is formed of aluminum oxide or silicon.

10. The device according to claim 1 wherein each cantilever element has a length of about 0.5 mm to 5 mm, a width of about 200 μm to 1 mm, and a thickness of about 50 μm to 500 μm.

11. The device according to claim 1, wherein the, first cantilever element has a surface that extends substantially parallel to a surface of the second cantilever element, and wherein said separating distance is on the order of hundreds of microns.

12. The device according to claim 11, wherein said surfaces are able to slide with respect to one another as a result of a movement of the first cantilever element with respect to the second cantilever element.

13. The device according to claim 11, wherein said separating distance is on the order of tens of microns.

14. The device, according to claim 1, wherein said actuating means includes providing a layer of active material on a surface of said at least one first cantilever element which is deformable upon application of an electrical or magnetic stimulus.

15. The device according to claim 14, wherein said active material is selected from the group consisting of piezoelectric materials and magnetostrictive materials.

16. The device according to claim 14, wherein said layer has a thickness of about 20 μm to 300 μm.

17. The device according to claim 14, wherein said actuating means includes a voltage source and electrodes for connecting said voltage source to said at least one first cantilever element.

18. The device according to claim 17, wherein said voltage source comprises an alternating or pulsed voltage source.

19. The device according to claim 1, wherein said sensing means includes providing a layer of active material on a surface of said at least one second cantilever element which generates a signal in response to said stress.

20. The device according to claim 19, wherein said sensing means includes a detection circuit and electrodes for connecting said detection circuit to said at least one second cantilever element.

21. The device according to claim 19, wherein said active material is selected from the group consisting of piezoelectric materials and magnetostrictive materials.

22. The device according to claim 19, wherein said layer has a thickness of about 20 μm to 300 μm.

* * * * *